United States Patent [19]

Lund

[11] Patent Number: 5,635,367

[45] Date of Patent: *Jun. 3, 1997

[54] METHOD FOR DETECTING STAPHYLOCOCCI

[75] Inventor: Marlys E. Lund, Eden Prairie, Minn.

[73] Assignee: Minnesota Mining and Manufacturing Company, St. Paul, Minn.

[*] Notice: The term of this patent shall not extend beyond the expiration date of Pat. No. 5,443,963.

[21] Appl. No.: 441,452

[22] Filed: May 15, 1995

Related U.S. Application Data

[63] Continuation of Ser. No. 189,182, Jan. 31, 1994, Pat. No. 5,443,963.
[51] Int. Cl.$^6$ .............................. C12Q 1/04; C12N 1/00
[52] U.S. Cl. .................... 435/34; 435/14; 435/29; 435/30; 435/39; 435/243; 435/805; 435/810; 435/882
[58] Field of Search ..................... 435/34, 14, 29, 435/30, 39, 243, 253.6, 261, 291, 299, 310, 805, 810, 882

[56] References Cited

U.S. PATENT DOCUMENTS

| Re. 24,906 | 12/1960 | Ulrich | 206/59 |
|---|---|---|---|
| 4,476,226 | 10/1984 | Hansen et al. | 435/299 |
| 4,565,783 | 1/1986 | Hansen et al. | 435/299 |
| 4,895,745 | 1/1990 | Velsley et al. | 428/40 |
| 5,089,413 | 2/1992 | Nelson et al. | 435/254 |
| 5,210,022 | 5/1993 | Roth et al. | 435/34 |
| 5,232,838 | 8/1993 | Nelson et al. | 435/30 |
| 5,393,662 | 2/1995 | Roth et al. | 435/38 |
| 5,424,122 | 6/1995 | Crandall et al. | 428/355 |

FOREIGN PATENT DOCUMENTS

| 0091837 | 10/1983 | European Pat. Off. |
|---|---|---|
| WO82/02563 | 8/1982 | WIPO . |

OTHER PUBLICATIONS

*Sigma*, Biochemical Organic Compounds for Research and Diagnostic Reagerb (Catalog), p. 182,1993.

Kloos et al., "Identification of *Staphylococcus* Species with the API STAPH–IDENT System", *Journal of Clinical Microbiology*, vol. 16, No. 3, Sep. 1982, pp. 509–516.

Geary et al., "Detection of phosphatase production by *Staphylococcus* species: a new method", *Medical Laboratory Sciences*, (1989) 46, pp. 291–294.

Arakawa et al., "Chemiluminescent Assay of Various Enzymes Using Indoxyl Derivatives as Substrate and Its Applications to Enzyme Immunoassay and DNA Probe Assay", *Analytical Biochemistry*, 199, pp. 238–242 (1991).

*Primary Examiner*—Cecilia J. Tsang
*Assistant Examiner*—Abdel A. Mohamed
*Attorney, Agent, or Firm*—Gary L. Griswold; Walter N. Kirn; James A. Rogers

[57] ABSTRACT

The present invention exploits the herein first reported, empirical observation that even though staphylococci produce the enzyme, beta-glucosidase, this genus of bacteria is not able to produce a metabolite that will enzymatically react with 5-bromo-4-chloro-3-indolyl-beta-D-glucopyranoside, a substrate commonly used to detect the presence of beta-glucosidase produced by other bacteria. In view of this unexpected observation, one embodiment of the present invention includes a selective medium containing inhibitors to enhance staphylococci growth as well as a first glucopyranoside substrate, such as 5-bromo-4-chloro-3-indolyl-beta-D-glucopyranoside, and a second phosphatase substrate, Such as 6-chloro-3-indolylphosphate or 5-bromo-6-chloro-3-indolylphosphate. In a particularly preferred embodiment of this invention, a thin film culture plate device, such as a PETRIFILM culture plate device, is prepared using a dry culture medium containing selected inhibitors, a first glucopyranoside substrate and a second phosphate substrate. When the thin film culture plate device is inoculated with a sample and then incubated for a sufficient period of time, staphylococci in the sample will produce colonies on the thin film device having a red color and other bacteria in the sample will produce colonies on the device having a blue color.

5 Claims, 1 Drawing Sheet

METHOD FOR DETECTING STAPHYLOCOCCI

This application is a continuation of U.S. application Ser. No. 08/189,182 filed Jan. 31, 1994, now U. S. Pat. No. 5,443,963.

The present invention relates to a method of detecting and/or enumerating bacteria in a sample and, more particularly, relates to a method of identifying and/or enumerating staphylococci in a mixed bacterial population using a novel indicator system.

BACKGROUND

A variety of methods and processes are currently available to determine, identify and enumerate bacteria in different types of samples. For example, methodologies are available to identify and enumerate coliform bacteria, coliforms, in samples of water, food or dairy products in order to assess the quality or potential contamination levels of those samples.

One approach to distinguish E. coli, a specific type of coliform bacteria commonly classified as a Gram-negative rod bacteria, from a mixed population of coliforms is reported in U.S. Pat. No. 5,210,022. In that patent, two substrates which form contrasting insoluble precipitates in the presence of two specific bacterial enzymes, beta-galactosidase and beta-glucuronidase, are incorporated in a test medium. The use of these two substrates allows coliforms to be differentiated from E. coli because all coliform bacteria produce beta-galactosidase while only E. coli produce beta-glucuronidase. As the different colonies of bacteria grow when incubated in the substrate-containing medium, contrasting colored precipitates form around either growing E. coli or coliform colonies. Identification of E. coli colonies from the other coliform colonies in the mixed population is readily made by the contrasting colors of the precipitated substrates.

A need for such selective differentiation exists for other kinds of bacteria which are pathogenic or which are associated with harmful effects in humans, such as Salmonella, staphylococci, or Streptococcus. Efficient methodologies to identify and enumerate staphylococci, commonly classified as a Gram-positive coccus bacteria, in food samples are particularly needed because staphylococcus enterotoxin associated with staphylococci contamination of chicken, other processed meats and dairy products is the agent responsible for most common cases of food poisoning.

Processes and products which allow for the identification and/or enumeration of such bacteria would provide significant benefit to a variety of industries including, but not limited to, manufacturers of food products, cosmetics and diagnostic assays.

SUMMARY OF THE INVENTION

This invention provides a method of identifying and/or enumerating staphylococci in a sample possibly contaminated with bacteria or potentially containing such bacteria. This method includes the steps of i) inoculating a selective medium with an aliquot of a sample, wherein the medium comprises inhibitors to promote the growth of staphylococci, a first substrate capable of producing an observable first color in the presence of beta-glucosidase and second substrate capable of producing a second color in the presence of phosphatase, ii) incubating the inoculated medium to produce bacterial colonies of sufficient size to allow visualization of the colonies in the presence of the first and second substrates in the medium, and iii) enumerating the colonies identified by the presence of the second color of the second substrate to give the number of staphylococci in the sample.

The present invention exploits the herein first reported, empirical observation that even though staphylococci produce the enzyme, beta-glucosidase, this genus of bacteria is not able to produce a metabolite that will enzymatically react with 5-bromo-4-chloro-3-indolyl-beta-D-glucopyranoside, a substrate commonly used to detect the presence of beta-glucosidase produced by other bacteria. In view of this unexpected observation, one embodiment of the present invention includes a selective solid medium containing inhibitors to enhance staphylococci growth as well as a first glucopyranoside substrate, such as 5-bromo-4-chloro-3-indolyl-beta-D-glucopyranoside, and a second phosphatase substrate, such as 6-chloro-3-indolylphosphate or 5-bromo-6-chloro-3-indolylphosphate. In this embodiment, staphylococci in a sample will produce metabolites that will react with the phosphatase substrate in the medium to produce colonies having red to red-violet color while other bacteria in the sample will produce beta-glucosidase that will react with the glucopyranoside substrate in the medium and produce colonies having a blue color.

In a particularly preferred embodiment of this invention, a thin film culture plate device, such as a PETRIFILM thin film culture plate, is prepared using a selective dry culture medium containing nutrients, selected inhibitors, a first glucopyranoside substrate and a second phosphatase substrate. When the thin film culture plate device is inoculated with a sample and then incubated for a sufficient period of time, staphylococci in the sample will produce colonies in the culture medium of the thin film device having a red color and other bacteria in the sample will produce colonies having a blue color.

The present invention provides an efficient, visual, colorometric method of identifying and enumerating staphylococci in a sample in a variety of solid media.

DETAILED DESCRIPTION

Figure 1:
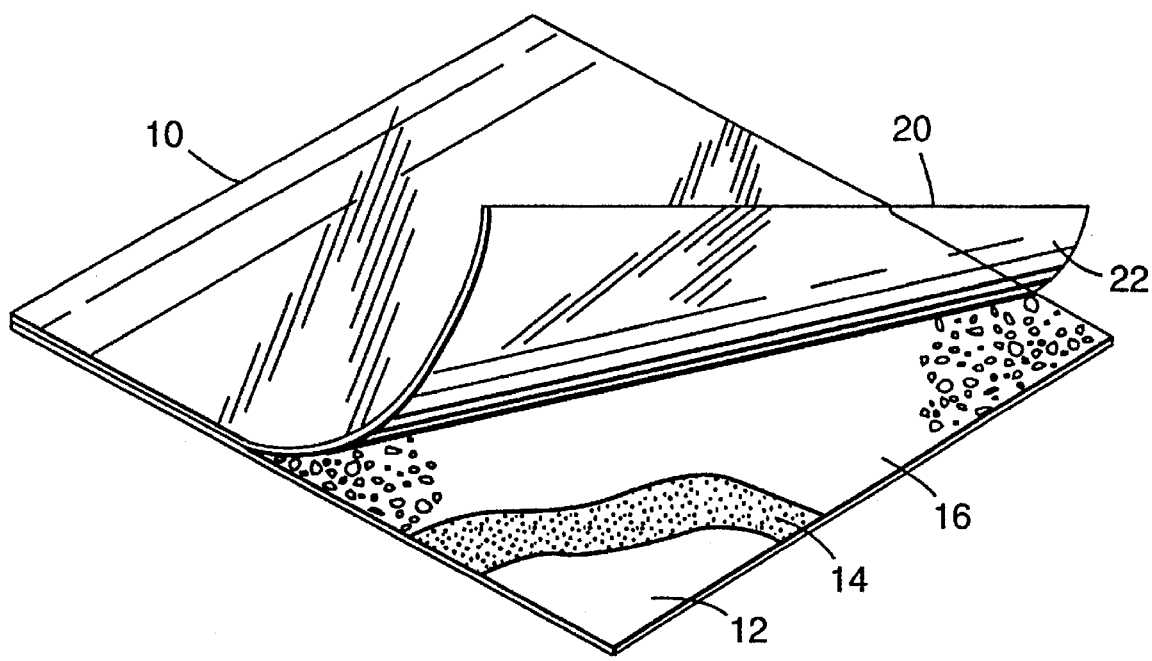
FIG. 1 is a top perspective view, partially in section, of a thin film culture device used to grow microorganisms.

The present invention exploits the herein first reported, empirical observation that even though staphylococci produce the enzyme, beta-glucosidase, this genus of bacteria is not able to produce a metabolite that will enzymatically react with 5-bromo-4-chloro-3-indolyl-beta-D-glucopyranoside, a substrate commonly used to detect the presence of beta-glucosidase produced by other bacteria. In view of this unexpected observation, one embodiment of the present invention includes a selective medium containing inhibitors to enhance staphylococci growth as well as a first glucopyranoside substrate, such as 5-bromo-4-chloro-3-indolyl-beta-D-glucopyranoside, and a second phosphatase substrate, such as 6-chloro-3-indolylphosphate or 5-bromo-6-chloro-3-indolylphosphate. In this embodiment, staphylococci in a sample will produce metabolites that will react with the phosphate substrate in the medium to produce colonies having red to red-violet color while other bacteria in the sample will produce beta-glucosidase that will react with the glucopyranoside substrate in the medium and produce colonies having a blue color.

A preferred selective media includes suitable nutrients, salts and ions needed for staphylococci to produce detectable colonies as well as inhibitors to prevent growth of other undesired microorganisms. Suitable nutrients, salts and ions include casein peptone, yeast extract, beef extract, glucose, sodium pyruvate, disodium phosphate, monopotassium phosphate, ferric ammonium titrate and sodium carbonate. Before use, the listed components are mixed or blended and then sterilized. Exposure to ethylene oxide, for example, is sufficient to sterilize the components. Selected inhibitors are also included in the medium to prevent the growth of undesired microorganisms including but not limited to Gram-negative bacteria such a *E. coli* as well as most Gram-positive bacteria. Inhibition of these undesired bacteria allows the growth of staphylococci to be selectively enhanced. Suitable inhibitors include a variety of well known antimicrobial or antibiotic compounds. For example, quinoline-based antibacterial compounds such as nalidixic acid, polymyxin-derived compounds such as colistin methanesulfonate and salts such as lithium chloride are known, preferred inhibitors.

The selective medium of this invention also includes two different substrates which allow visual detection of different types of growing colonies. One substrate is a glucopyranoside substrate which will react with a beta-glucosidase metabolite produced by bacteria, except bacteria of the genus staphylococci, to produce a detectable substrate. Preferably the detectable substrate is a colored, visually detectable substrate. A variety of known beta-glucosidase-indicating compounds are commercial available. Typical amounts of these substrates which may used in the selective medium range from about 25–500 mg/ml and preferably range from about 25–50 mg/ml. Suitable beta-glucosidase indicators include 5-bromo-4-chloro-3-indolyl-beta-D-glucopyranoside which provides a blue precipitate in the presence of beta-glucosidase and 4-methyhmbelliferyl-β-D-glucopyranoside which provides a detectable fluorescent substrate in the presence of beta-glucosidase.

A second substrate is an indolylphosphatase substrate that will react with a phosphatase metabolite produced by staphylococci to produce a detectable, preferably precipitated, substrate. Commercially available phosphatase indicators include 6-chloro-3-indolylphosphate or 5-bromo-6-chloro-3-indolylphosphate which react with staphylocci phosphatase to provide a red to red-violet colored, precipitated substrate. Typically amounts of phosphatase substrates which may be used in the selective medium range from about 100–500 mg/ml and preferably range from about 200–300 mg/ml.

The selective medium of the present invention is generally mixed with gel-forming materials to give a solid medium. A solid medium provides a defined area for growth of bacterial colonies which may be present in a sample. Suitable gel-forming materials include commercially available agar as well as methyl pectin which is described in U.S. Pat. No. 5,210,022. Other gelling materials which are preferred for use in thin film culture plate devices include gel-forming gums such as xanthan gum, locust bean gum, rhamsan gum and guar gum or mixtures thereof.

When the present selective media is used, a sample is typically diluted with a diluent and then used to inoculate the solid medium. The inoculated medium is then incubated for about 40–56 hours and the medium is then visually inspected. Staphylococci which are present in a sample will produce colonies which react with the phosphatase substrate in the medium to provide red to red-violet colored zones while other bacteria in the sample will produce colonies which produce beta-glucosidase that will react with the glucopyranoside substrate in the medium and provide blue colored zones.

In a particularly preferred embodiment of this invention, a thin film culture plate device, essentially similar to an Aerobic Count PETRIFILM culture plate device (commercially available form 3M, St. Paul, Minn., catalog number 6400) is prepared using a dry culture medium containing selected inhibitors, a first glucopyranoside substrate and a second phosphate substrate. When the thin film culture plate device is inoculated with a sample and then incubated for a sufficient period of time, staphylococci in the sample will produce colonies on the thin film device having a red color and other bacteria in the sample will produce colonies on the device having a blue color.

FIG. 1 illustrates a thin film culture plate device suitable for use with the present invention. Such thin film culture devices are described in U.S. Pat. Nos. 4,565,783, 5,089,413 and 5,232,838 which are all incorporated by reference in this application for the purposes of describing the processes of making and using these types of thin film culture plate devices.

Briefly, a dry culture device 10 includes a body member having a self-supporting, waterproof substrate 12. Substrate 12 is preferably a relatively stiff material made of a waterproof polymer that does not absorb water such as polyester, polypropylene, or polystyrene. Other suitable waterproof materials include substrates such as paper containing a waterproof polyethylene coating.

The upper surface of substrate 12 is coated with a layer of adhesive 14, such as isooctyl acrylate/acrylamide in a weight ratio of 96/4 or an aqueous emulsion suspension of a copolymer of isooctyl acrylate and N-vinylpyrrolidone at a 98:2 weight ratio described in U.S. Pat. No. 5,232,838 as well as IGEPAL CA 897 nonionic surfactant and lauroyl peroxide, which serves to hold a cold-water soluble dry powder 16 that is a mixture of a dry gelling agent and microbial growth nutrients adhered in a uniform layer on the substrate. The adhesive must not inhibit the growth of the microorganisms. In addition, the adhesive should be sufficiently transparent when hydrated to allow viewing of bacterial colonies growing on the surface of the substrate through the coated substrate. The adhesive 14 should also be coated on the substrate in a thickness which allows the substrate to be uniformly coated with powdered gelling agents and nutrients without completely embedding such particles in the adhesive.

A layer of cold-water soluble dry powder 16 is uniformly adhered to the adhesive layer 14. Preferably, the soluble powder contains gelling agents and microbial growth nutrients. Suitable gelling agents include both natural and synthetic agents which form solutions with water at room temperature. These gelling agents include hydroxyethylcellulose, carboxymethyl cellulose, polyacrylamide, or algin. A preferred mixture of gelling agents or gums includes xanthan gum, locust bean gum, rhamsan gum and guar gum. Suitable nutrients for use in the present invention also include nutrients which are soluble in water at room temperature. The specific types of nutrients are selected in order to promote the growth of the microorganisms which will be grown on the substrate 12. A variety of nutrients may be used which include components such as carbohydrates, proteins and minerals. A preferred nutrient powder includes casein peptone, yeast extract, glucose, ferric ammonium citrate, sodium pyruvate, sodium carbonate and guar gum mixed with the water-based copolymer of isooctyl acrylate and N-vinylpyrrolidone adhesive. Additional components include salts and minerals such as sodium pyruvate, monobasic potassium phosphate, dibasic potassium phosphate as well as inhibitors such as colistin methanesulfonate, lithium chloride and nalidixic acid.

In the device illustrated in FIG. 1, a cover sheet 20 is attached to one edge of an upper surface of the substrate 12. Cover sheet 20 is preferably made of a transparent film or sheet material in order to facilitate counting of bacterial colonies present on the substrate. In addition, cover sheet 20 is preferably impermeable to bacteria and water vapor in order to avoid the risk of contamination and deterioration of the components. A preferred material for use as a cover sheet 20 is biaxially-oriented polypropylene.

A layer of a water-insoluble adhesive containing an indicator dye is applied on the surface of cover sheet 20 that is adjacent to substrate 12. Suitable adhesives 22 which are applied to cover sheet 20 include acrylate based adhesives such as the adhesives described in U.S. Pat. No. 4,565,783 and U.S. Pat. Re No. 24,906 as well as an adhesive copolymer of isooctyl acrylate and acrylic acid in a 98:2 weight ratio. Preferred adhesives are generally water-insoluble isooctyl acrylate-based adhesives which will not detrimentally interfere with, or hamper the growth of, microorganisms such as bacteria. The cover sheet also includes a beta-glucosidase substrate such as 5-bromo-4-chloro-3-indolyl-β-D-glucopyranoside and a phosphatase substrate such as 5-bromo-6-chloro-3-indolylphosphate. If desired, additional gelling agents or nutrients may also be adhered to the adhesive that is applied to the surface of cover sheet 20.

In use, a predetermined amount of inoculum, typically about one milliliter of inoculum, is added to a device illustrated in FIG. 1 by pulling back cover sheet 20 and adding an aqueous test sample or water to the middle of substrate 12. Cover sheet 20 is then replaced over substrate 12 and the inoculum is evenly spread on the substrate using a weighted circular template which is used to confine the inoculum to a specific area of substrate 12. As the inoculum contacts and is spread on substrate 12, the gelling agents and nutrients adhered to substrate 12 hydrate to form a growth-supporting nutrient gel. The inoculated device is then incubated for a predetermined time after which the number of bacterial colonies growing on the substrate may be counted through the transparent cover sheet 20.

The following examples are provided to further illustrate the practice of various embodiments of the present invention. The examples are provided for illustrative purposes only and should not be construed to limit the scope of the invention which is set out in the appended claims.

EXAMPLES

Example 1

One side of 0.13 mm thick polyethylene-coated paper (Schoeller Paper Inc., of Pulaski, N.Y.) was coated with a noninhibitory adhesive copolymer of isooctyl acrylate (IOA) and acrylamide at a 98:2 weight ratio (IOA:ACM) at a level (measured when dry) of 0.93 rag/cm$^2$ and dried.

The adhesive was then dusted uniformly with a mixture of 2 parts by weight guar gum (Meyhall Chemical AG, Kreuzlingen, Switzerland) and 1 part of a nutrient mixture containing in parts by weight: casein peptone 5 parts, yeast extract 2.5 parts, glucose 1 part, sodium pyruvate 10 parts, beef extract 1 part, disodium phosphate 2 parts, and monopotassium phosphate 0.7 parts. This powder-coated paper was disinfected by exposure to ethylene oxide.

A cover sheet was made from a sheet of 0.04 mm thick, transparent, biaxially-oriented, corona-treated polypropylene film, coated with a noninhibitory adhesive copolymer of isooctyl acrylate (IOA) and acrylic acid (AA) in a 98:2 weight ratio (IOA:AA), at a level (measured when dry) of 0.93 mg/cm$^2$, and dried. The adhesive was then dusted uniformly with a mixture of 2 parts by weight xanthan gum (KELTROL gum, available from Kelco Inc., San Diego, Calif.), 2 parts locust bean gum (GENU gum, available from Hercules, Inc., Wilmington, Del.), 1 part rhamsan gum (K1A 112 available from Kelco Inc.) and 1 part M150 guar gum (MEYPROGAT gum, Meyhall Chemical AG). The excess powder was shaken loose. The powders had previously been disinfected by exposure to ethylene oxide or gamma irradiation.

Both the adhesive-coated and powder-coated bottom portion and cover sheet were cut into 7.6 cm×10.2 cm pieces, placed together with the powdered sides facing each other, and heat-sealed together along one edge.

In use, the device was placed on a level surface, and the top cover sheet folded back, exposing the powder-coated surface of the bottom section of the device. A 1 ml aqueous test sample containing a solution (prepared as described below) of a mixture of substrate and bacteria was carefully placed in the center of the bottom section of the device, and the cover sheet replaced, powder-coated side down. A weighted spreader was applied to evenly spread the aqueous test sample over the powder-coated surfaces of the culture media device. The inoculated device was placed in an incubator and incubated in the normal manner at 35° C. After incubation, the device was read just as with a standard pour-plate.

Solutions of substrate and bacteria were prepared as follows: 10.1 mg of 6-chloro-3-indolyl-β-D-glucopyranoside para-toluidine salt was dissolved in 100 µl of N,N-dimethylformamide. When 400 µl of ethanol was added, a precipitate formed, therefore 200 µl of additional N,N-dimethylformamide was added. To 10.2 mg of 6-chloro-3-indolylphosphate para-toluidine salt and 6-chloro-5-bromo-3-indolylphosphate para-toluidine salt respectively, both dissolved in 300 µl of N,N-dimethylformamide was added 400 and 200 µl of ethanol, respectively. 9.9 mg of 5-bromo-4-chloro-3-indolyl-β-D-glucopyranoside para-toluidine salt (available from Biosynth International Inc., Skokie, Ill.) was dissolved in 200 µl of N,N-dimethylformamide and 300 µl of ethanol.

Three colonies each of *Staphylococcus aureus* and *Streptococcus faecalis* growing on sheep's blood agar plates and derived from cultures ATCC 29213 and ATCC 29212 respectively were picked with the PROMPT inoculation system No. 6314 (available from Baxter Scientific Products, Catalog No. B1026-10D) to provide bacterial suspensions which were subsequently diluted 1/10,000 with Butterfield's buffer.

Four 10 ml portions of each bacterial suspension in buffer were transferred into each of 4 sterile tubes to provide a total of 8 tubes. To separate tubes of each bacterium was added an aliquot of the substrate solution prepared above as shown below:

140 µl of 6-chloro-3-indolyl-β-D-glucopyranoside salt (substrate A)

100 µl of 5-bromo-4-chloro-3-indolyl-β-D-glucopyranoside salt (substrate B)

140 µl of 6-chloro-3-indolylphosphate salt (substrate C) and

100 µl of 6-chloro-5-bromo-3-indolylphosphate salt (substrate D)

Four mixtures were prepared by combining 1 ml of the *S. aureus* and 6-chloro-3-indolylphosphate mixture with 1 ml of the *S. faecalis* and 5-bromo-4-chloro-3-indolyl-β-D-glucopyranoside mixture; 1 ml of the *S. aureus* and 6-chloro- 5-bromo-3-indolylphosphate mixture with 1 ml of the *S. faecalis* and 5-bromo-4-chloro-3-indolyl-β-D-glucopyranoside mixture; 1 ml of the *S. faecalis* and 6-chloro-3-indolylphosphate mixture with 1 ml of the *S. aureus* and 5-bromo-4-chloro-3-indolyl-β-D-glucopyranoside mixture and 1 ml of the *S. faecalis* and 6-chloro-5-bromo-3-indolylphosphate mixture with 1 ml of the *S. aureus* and 5-bromo-4-chloro-3-indolyl-β-D-glucopyranoside mixture. It was observed that all of the mixtures showed some cloudiness, indicating precipitation.

One milliliter of each of the twelve substrate-bacteria suspensions was used to inoculate twelve of the culture media devices prepared as described above. The devices were incubated at 35° C. The results were observed after 24 hours of incubation.

TABLE 1

| Bacteria | Substrate | Results |
|---|---|---|
| S. aureus | A | No colonies observed |
| S. aureus | D | Dark compact purple colonies |
| S. aureus | C | Lighter more diffuse purple colonies |
| S. aureus | B | No colonies observed |
| S. faecalis | C | Pale diffuse purple colonies |
| S. faecalis | D | Slightly darker more compact purple colonies |
| S. faecalis | A | No colonies observed |
| S. faecalis | B | Intense somewhat diffuse blue-green colonies |
| S. aureus/S. faecalis | C, B | Mixed blue-green & purple colonies |
| S. aureus/S. faecalis | D, B | Mixed blue-green & purple colonies |
| S. aureus/S. faecalis | B, C | Mixed blue-green & purple colonies |
| S. aureus/S. faecalis | B, D | Mixed blue-green & purple colonies |

Surprisingly, the *S. aureus* did not metabolize the indicator when the substrate was solely a glucopyranoside as shown by the lack of colored colonies. The *S. faecalis* produced colored colonies on the 5-bromo-4-chloro-3-indolyl-β-D-glucopyranoside substrate, indicating a clear difference in the ability of these bacteria to use that substrate.

Example 2

Demonstration of Lack of beta-Glucosidase Activity by Staphylococcus Variants

*Staphyococcus aureus* variants were obtained from the Centers For Disease Control, Atlanta, Ga. and maintained as part of a private collection at Minnesota Mining and Manufacturing Company (3M, St. Paul, Minn.) were tested for β-D-glucosidase activity using three systems, agar, broth and PETRIFILM thin film culture medium devices (described in Example 1). The agar contained 5-bromo-4-chloro-3-indolyl-β-D-glucopyranoside (x-glucoside) as the substrate. The conventional buffered peptone broth (available from Difco, Detroit, Mich.) was carbohydrate free and was tested using 5-bromo-4-chloro-3-indolyl-β-D-glucopyranoside or 4-methylumbelliferyl-β-D-glucopyranoside (4-MUG) (solutions prepared as described in Example 1) as substrates. The PETRIFILM culture plate devices were prepared as described in Example 1 and were tested by plating as described in Example 1 on the culture plate devices using either x-glucoside and 6-chloro-5-bromo-3-indolylphosphate para-toluidine salt (phosphate) (solutions prepared as described in Example 1) as substrates. As shown in Table 2, *S. aureus* variants grown on the agar plates failed to use the x-glucoside substrate, the colonies remaining off-white to golden rather than turning the intense blue seen with Streptococci although the same variants all used the 4-MUG substrate. All 32 *S. aureus* variants in broth metabolized the 4-MUG substrate but failed to metabolize the x-glucoside substrate. All 32 *S. aureus* variants grew as purple colonies on the PETRIFILM culture plate devices using 6-chloro-5-bromo-3-indolylphosphate substrate but failing to metabolize the x-glucoside substrate.

The identity of both purple and blue-green colonies present on the PETRIFILM culture plate devices was confirmed by streaking colonies of each bacterium to sheep's blood agar plates and reidentifying the pure cultures of bacteria by conventional methods.

TABLE 2

| Organism | Broth with 4-MUG Substrate | Broth with X-Glucoside Substrate | Agar with 4-MUG Substrate | Agar with X-Glucoside Substrate | Petrifilm with 4-MUG Substrate | Petrifilm with X-glucoside Substrate |
|---|---|---|---|---|---|---|
| S. faecalis control (88) | + | + | NA | NA | + | + |
| coagulase negative Staph control | − | − | −/+* | | − | − |
| S. aureus - 76, 77, 78, 79, 80, 81, 82, 83, 84, 85, 86, 87, 1043, 1052, 1054, 1060, 1068, 1070, 1072, 1078, 1081, 1112, 1117, 1119, 1120, 1154, 1155, 1156, 1166, 1167, 1168, 2013 | + | − | + (weak) | − | + | − |
| Entero-coccus controls (10 strains) | NA | NA | all + | all + | NA | NA |

*10 strains were used, 8 were negative, 2 were positive

Example 3

Using thin film culture media devices prepared as described in Example 1, the presence of staphylococci in foods was evaluated in comparison with Baird-Parker agar as described below.

Stressed staphylococci were prepared to simulate actual "real life" conditions by growing *Staphylococcus aureus* strain 1060 overnight in trypticase soy broth (available from BBL Microbiological Systems, Cockeyesville, Md.). A 0.01 ml sample of this broth culture was pipetted into 10 ml of 0.1M, pH 7.2 phosphate buffer prewarmed to 52° C. This mixture was incubated at 52° C. for 20 minutes, then diluted with Butterfield's buffer for plating. The dilution used was 1:100 (mixture:buffer). This buffer was stored at 4° C. then warmed to room temperature and used hereinafter.

The water-based adhesive composition to be coated on polyethylene paper as described in Example 1 was formed by dissolving 500 g of nutrient powder consisting of 132 parts of casein peptone, 66 parts of yeast extract, 26 parts of glucose, 5.8 parts of ferric ammonium citrate, 264 parts of sodium pyruvate and 5.8 parts of sodium carbonate plus 75 g of M150 guar gum in 5 kg of adhesive. The adhesive similar to that described in Example 1 was an aqueous emulsion suspension of a copolymer of isooctyl acrylate (IOA) and N-vinylpyrrolidone (NVP) at a 98:2 weight ratio (IOA:NVP) with IGEPAL CA 897 nonionic surfactant and lauroyl peroxide to which had been added a stirred aqueous solution of 0.2503 parts colistin methanesulfonate, 175 parts of lithium chloride and 2450 parts of distilled water to which had been added a solution of 0.4001 parts of nalidixic acid which had been dissolved in 50 parts water by the addition of a small amount of 10N sodium hydroxide solution and 0.075 parts of methyl-$\beta$-D-glucoside.. The coated substrate was dried in an air oven at about 90° C. to yield a sticky layer on the surface of the substrate at a dry weight of 3.55 to 4.2 mg/cm$^2$.

A mixture of cold-water-soluble powders including one part nutrient powder and two parts mixed gums powder formed of proportions by weight of 2 parts of xanthan gum (KELTROL gum, 2 parts of locus bean gum (MYPRODYNE gum), 1 part of K1A 112 and 1 part of M150 guar gum, was dusted over the surface of the water-based adhesive layer. Any excess powder was shaken loose. This adhesive-coated and powder-coated paper was used to form the bottom portion of the culture media device.

Cover sheets were made from sheets of 0.04 mm thick, transparent, biaxially-oriented, corona-treated polypropylene film, coated with an adhesive copolymer of isooctyl acrylate (IOA) and acrylic acid (AA) in a 98:2 weight ratio (IOA:AA), at a level (measured when dry) of 0.969 to 1.29 mg/cm$^2$, and containing 0.66 g of 5-bromo-4-chloro-3-indolyl-$\beta$-D-glucopyranoside and 5.43 g of 5-bromo-6-chloro-3-indolylphosphate in 1.2 liters of methanol and 1.2 liters of acetone per 3 kg of adhesive polymer and the adhesive composition was dried. The cover sheets were dusted with the mixed gums powder.

A mixture of 9 ml of S. aureus in Butterfield's buffer and 1 ml of food sample was prepared to be used to inoculate the culture plate devices. The foods used were chicken and cheddar, Monterey jack, swiss and mozzarella cheeses diluted 1 to 10 with water. Duplicate 1 ml portions were applied to culture plate devices, quadruplicate 0.5 ml portions were applied to freshly prepared Baird-Parker agar.

Undiluted pure S. aureus and S. aureus diluted to 1:10 were used to inoculate positive control culture plates. All of the samples were incubated at 35° C. and media counts were taken at 40 hours. The results are summarized in Table 3.

TABLE 3

| | Mean Counts (cfu/ml) | | |
|---|---|---|---|
| | Baird-Parker | Magenta PO$_4$* | Productivity Magenta |
| Pure Staph-10° | 144.5 | 163.5 | 113% |
| Pure Staph-10$^{-1}$ | 15.5 | 13 | 84% |
| Cheddar | 173.5 | 212 | 122% |
| Swiss | 160 | 173.5 | 108% |
| Mozzarella | 193 | 195 | 101% |
| Monterey Jack | 196.5 | 191 | 97% |
| Chicken | 226 | 195.5 | 87% |

*5-bromo-6-chloro-3-indolylphosphate gives a bright magenta color and is a preferred phosphate substrate.

Productivity is a comparison of the method and device of the invention to the Baird-Parker agar, a well-known standard. S. aureus colonies are bright magenta in the device of the invention. The results show that the number of colony forming units are about the same using both methods.

I claim:
1. A thin film culture plate device for identifying and enumerating staphylococci in a sample containing more than one species of bacteria, comprising:

i) a self-supporting, waterproof substrate to which is adhered a rehydratable selective medium powder containing nutrients, inhibitors to promote the growth of staphylococci, and at least one gelling agent, and ii) a transparent cover sheet having a layer of adhesive consisting essentially of a dual substrate system having an indolylglucopyranoside substrate which provides a visible first color change in the presence of beta-glucosidase and a phosphate substrate which provides a visible second color change in the presence of staphylococci and at least one gelling agent.

2. The device of claim 1 wherein the inhibitors are selected from the group consisting of colistin methanesulfonate, nalidixic acid and lithium chloride.

3. The device of claim 1 wherein the indolylglucopyranoside substrate is 5-bromo-4-chloro-3-indolyl-beta-D-glucopyranoside.

4. The device of claim 1 wherein the phosphate is selected from the group consisting of 6-chloro-3-indolylphosphate and 5-bromo-6-chloro-3-indolylphosphate.

5. The device of claim 1 wherein the gelling agent is selected from group consisting of xanthan gum, locust bean gum, rhamsan gum and guar gum.

* * * * *

UNITED STATES PATENT AND TRADEMARK OFFICE
CERTIFICATE OF CORRECTION

PATENT NO.: 5,635,367
DATED: June 3, 1997
INVENTOR(S): Marlys E. Lund

It is certified that error appears in the above-identified patent and that said Letters Patent is hereby corrected as shown below:

Col. 3, Line 5, delete the word "titrate" and insert in place thereof --citrate--.

Col. 9, Line 31, delete the word "locus" and insert in place thereof --locust--.

Signed and Sealed this

Twentieth Day of April, 1999

Attest:

Q. TODD DICKINSON

Attesting Officer

Acting Commissioner of Patents and Trademarks